(12) United States Patent
Perkins

(10) Patent No.: US 8,545,444 B2
(45) Date of Patent: Oct. 1, 2013

(54) SYSTEM AND METHOD FOR PAIN-FREE INJECTIONS

(76) Inventor: Walter T. Perkins, South Riding, VA (US)

(*) Notice: Subject to any disclaimer, the term of this patent is extended or adjusted under 35 U.S.C. 154(b) by 239 days.

(21) Appl. No.: 13/028,227

(22) Filed: Feb. 16, 2011

(65) Prior Publication Data

US 2012/0209246 A1    Aug. 16, 2012

(51) Int. Cl.
*A61M 5/00* (2006.01)

(52) U.S. Cl.
USPC ............ 604/115; 604/112; 604/116; 607/63; 607/149

(58) Field of Classification Search
USPC ................ 604/503, 506, 511, 512, 513, 112, 604/179, 115, 116; 607/46, 47, 63, 149; 600/554, 557
See application file for complete search history.

(56) References Cited

U.S. PATENT DOCUMENTS

| | | | |
|---|---|---|---|
| 3,620,209 A * | 11/1971 | Kravitz | ............................ 601/79 |
| 4,147,171 A | 4/1979 | Greene et al. | |
| 4,292,980 A | 10/1981 | Suzuki | |
| 4,431,000 A | 2/1984 | Butler | |
| 4,556,064 A | 12/1985 | Pomeranz et al. | |
| 5,067,495 A | 11/1991 | Brehm | |
| 5,350,414 A | 9/1994 | Kolen | |
| 5,458,625 A | 10/1995 | Kendall | |
| 5,496,363 A | 3/1996 | Burgio et al. | |
| 5,533,514 A | 7/1996 | Lavigne et al. | |
| 5,580,350 A | 12/1996 | Guibert et al. | |
| 5,643,329 A | 7/1997 | Solomonow et al. | |
| 5,935,156 A | 8/1999 | Chandler et al. | |
| 5,995,873 A | 11/1999 | Rhodes | |
| 6,044,303 A | 3/2000 | Agarwala et al. | |
| 6,662,051 B1 | 12/2003 | Eraker et al. | |
| 6,721,603 B2 | 4/2004 | Zabara et al. | |
| 6,988,006 B2 | 1/2006 | King et al. | |
| 7,200,443 B2 | 4/2007 | Faul | |
| 7,386,349 B2 | 6/2008 | Davar | |
| 7,813,803 B2 | 10/2010 | Heruth et al. | |
| 2004/0015188 A1 | 1/2004 | Coulter | |
| 2005/0246006 A1 | 11/2005 | Daniels | |
| 2008/0188779 A1 * | 8/2008 | Vallero | ............................ 601/21 |

* cited by examiner

*Primary Examiner* — Bhisma Mehta
(74) *Attorney, Agent, or Firm* — Dale B Halling

(57) ABSTRACT

A system for administering pain-free injections includes an electric current source having at least two electrodes attached adjacent an injection site, the electric current source producing a variable numbness pattern and providing a frame of reference for identifying a plurality of sub-areas of the injection site; and a probe applied to the plurality of sub-areas of the injection site for pain-response testing, wherein one or more areas of numbness in the variable numbness pattern are identifiable according to the plurality of sub-areas of the injection site. A fence may be removably applied to the injection site and provide a frame of reference for identifying a plurality of sub-areas of the injection site, and may aid in identifying one or more areas of numbness in the variable numbness pattern. The fence may be removably applied to the injection site via a belt or manual pressure.

8 Claims, 5 Drawing Sheets

SYSTEM AND METHOD FOR PAIN-FREE INJECTIONS

I. FIELD OF THE INVENTION

The present invention relates to injections via hypodermic needles, especially to a system and method for pain-free injections.

II. BACKGROUND OF THE INVENTION

For many people, injections via hypodermic needles are painful. For some, the pain may be debilitating to the point where medically-beneficial treatments are delayed or avoided. A superficial review of the Internet reveals the seriousness of the problem and the amount of time devoted to solving it. Numerous and varied solutions have been proposed, including slapping, pinching or even local or topical analgesics or ice to numb the area or to simply distract the recipient of the injection. Of course, distractions are not effective when the injections are self-administered.

Transcutaneous electrical nerve stimulator machines (TENS) have been available on the market for several decades, and promise a modern solution to the old problem of painful injections. TENS machines deliver small electrical pulses to the body via electrodes placed on the skin. TENS machines are thought to affect the way pain signals are sent to the brain via nerves and the spinal cord in a manner which provides temporary numbness. TENS machines are able to deliver electric current through the skin to the nerves under the skin, and the electric power may be able to be manipulated so that various wave forms, amplitudes, current flow, voltages and other parameters can be delivered to reduce the ability of the nerves to sense pain. TENS machines are thought to work in two ways:

When the machine is set on a high pulse rate, such as 92-130 hertz, it is thought to trigger the "pain gate" to close. The "pain gate" comes from the gate theory of pain, which is predicated on the idea that when certain nerves are stimulated these can interfere with, or close, the gate on signals from nerves that transmit pain. The application of this "gate theory" describes the normal method of use of a TENS machine.

In a second manner of operation, the TENS machine is set on a low pulse rate, such as 2 to 5 Hertz, in order to stimulate the body to make its own pain-easing chemicals, which are called endorphins. These endorphins provide a morphine-like activity to block pain signals.

Research trials and independent tests which have studied the use of TENS machines have provided conflicting results as to how well they generally work, and how much pain relief they provide. Some conclude that they are not effective at all. Others conclude that they seem to help some people, perhaps as well as a placebo. However, the amount of pain relief provided varies greatly from person to person, even under the same conditions.

TENS devices are relatively inexpensive, commonly available and provide hope for new generations of pain sufferers, which explains their prevalence in the market place despite the lack of positive evidence as to their efficacy.

Numerous variations of TENS machines are on the market or have been developed over the last few decades, the proponents of each new model pointing to the poor performance of those coming before.

III. SUMMARY OF THE INVENTION

The object of the present invention is to provide a system and method for administering pain-free injections, both self-administered injections and those administered by others. The system offers a cost- and performance-effective method for providing localized numbness or analgesic fields for medical or body-decorating purposes.

A first embodiment of the invention, a system for administering pain-free injections includes an electric current source having at least two electrodes attached adjacent an injection site, the electric current source producing a variable numbness pattern and providing a frame of reference for identifying a plurality of sub-areas of the injection site; and a probe applied to the plurality of sub-areas of the injection site for pain-response testing, wherein one or more areas of numbness in the variable numbness pattern are identifiable according to the plurality of sub-areas of the injection site.

The application of the probe to the sub-areas of the injection site permits the user to identify the variable and unpredictable numb or desensitized areas in the injection site. Selection and use of one or more of these numb areas provides a pain-free injection site.

A second embodiment of the invention, a system for use in administering pain-free injections includes an electric current source having at least two electrodes attached adjacent to an injection site, the electric current source producing a variable numbness pattern; a fence or frame removably applied to the injection site and providing a frame of reference for identifying a plurality of sub-areas of the injection site; and a probe applied to the plurality of sub-areas of the injection site, wherein one or more areas of numbness in the variable numbness pattern are identifiable according to the sub-areas defined by the fence.

According to a further embodiment of the invention, the electric current source is a transcutaneous electrical nerve stimulation (TENS) device. The use of a TENS device provides an advantage in that a ready supply of various TENS devices are available in the marketplace, each performing in approximately the same manner, and each having the same limited efficacy.

According to a further embodiment of the invention, the electrodes of the electric current source are attached to the fence. This arrangement provides the advantage of a consistent spacing arrangement of the electrodes. A pre-defined spacing arrangement avoids the health risks associated with electrodes that are too close together and further avoids the measurable loss of efficacy when the electrodes are too far apart.

In another embodiment of the invention, the fence is removably applied to the injection site via a belt. A belt or strap provides an advantage in that a secure fence arrangement makes the use of the fence more predictable and the identification of areas of numbness more certain.

In another embodiment of the invention, the fence is removably applied to the injection site via manual pressure. The manual pressure provides an advantage in that the fence is quickly and easily adjustable for optimal placement and the location of the unpredictable areas of numbness.

In a further embodiment of the invention, the fence is a generally linear element. The linear element provides an advantage of a defined area that is very open so as to provide minimal possible interference in selecting a numb injection site within the sub-areas defined by the fence.

In yet a further embodiment of the invention, the fence is a polygonal framework. The polygonal framework provides the advantage of a regular, well-defined area that provides easy visualization cues for subsequent injections when a numb location is found.

In another embodiment of the invention, the fence includes a graduated scale. The graduated scale provides the advantage of a very precisely-defined area that provides easy visualization cues for subsequent injections when a numb location is found.

In a further embodiment of the invention, the fence includes a shield wall, which blocks a view of at least a part of the injection site. The wall provides an advantage of a blind zone which is helpful to those who might be a bit squeamish about injections, both the self-administered injections and those by others.

In a further embodiment of the invention, the fence includes indicia regarding suggested placement of positive and negative electrodes of the electric current source. The indicia provide the advantage of a more consistent set up of the system, and more consistent results, despite the unpredictable performance of TENS devices.

In another embodiment of the invention, the fence includes body-conforming contours which provide the advantage of more secure fence placement regardless of how the fence is held in place.

According to a further embodiment of the invention, the fence and probe include medical-grade materials, either plastics, metals or select soft composites. This provides the advantage of construction that is rugged enough to withstand repeated sterilization cycles and regular use without undue wear.

According to a further embodiment of the invention, the probe is most simply comprised of a shaft or handle for grasping it, and a sharp end. It can resemble a toothpick or pencil or similar device for manipulation of a pointed end. Any acceptable arrangement provides a generally cylindrical or polygonal shape having a pointed tip at least one end. This arrangement provides an advantage in that the probe is easily controlled by a user, and permits a user to test the pointed tip of the probe at various areas of the injection site for areas of numbness, but without puncturing the injection site. The pointed end may have a hilt or other design feature to discourage the perforation of the skin.

According to another aspect of the invention, a method for administering pain-free injections comprises the steps of attaching at least two electrodes of an electric current source adjacent an injection site; producing a variable numbness pattern in the injection site with the electric current source; providing a frame of reference with the electrodes for identifying a plurality of sub-areas of the injection site; sequentially applying a probe to the plurality of sub-areas of the injection site; and identifying one or more areas of numbness in the variable numbness pattern according to the plurality of sub-areas.

According to a further aspect of the invention, a method for administering pain-free injections comprises the steps of attaching at least two electrodes of an electric current source adjacent an injection site; producing a variable numbness pattern in the injection site with the electric current source; removably applying a fence to the injection site and providing a frame of reference for identifying a plurality of sub-areas of the injection site; sequentially applying a probe to the plurality of sub-areas of the injection site; and identifying one or more areas of numbness in the variable numbness pattern according to the sub-areas defined by the fence.

According to a further embodiment of the invention, the method may include the step of administering a pain-free injection in at least one of the areas of numbness identified by the probe as being numb, or according to its fence-defined location.

IV. BRIEF DESCRIPTION OF THE DRAWINGS

Figure 6A:
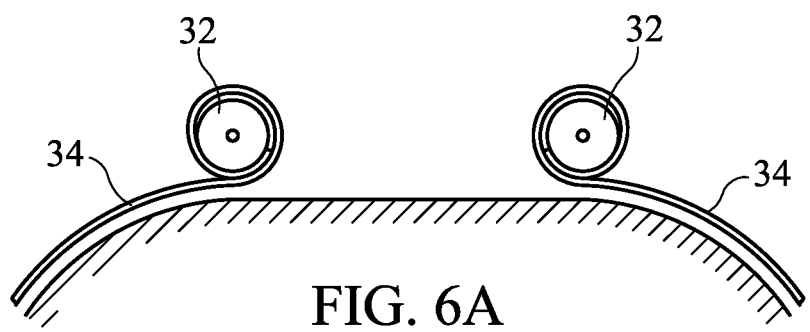
Figure 6B:
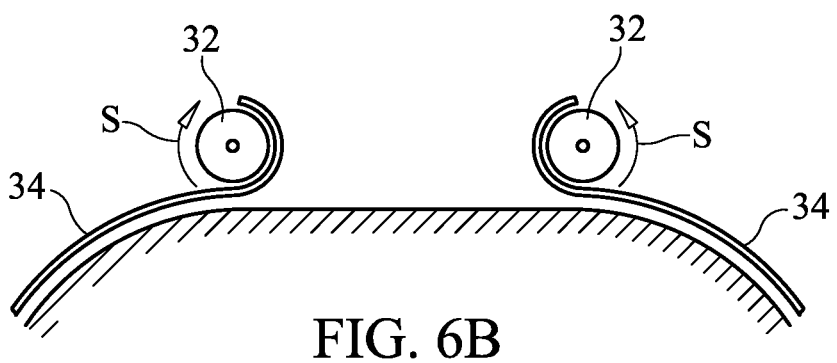
Figure 6C:
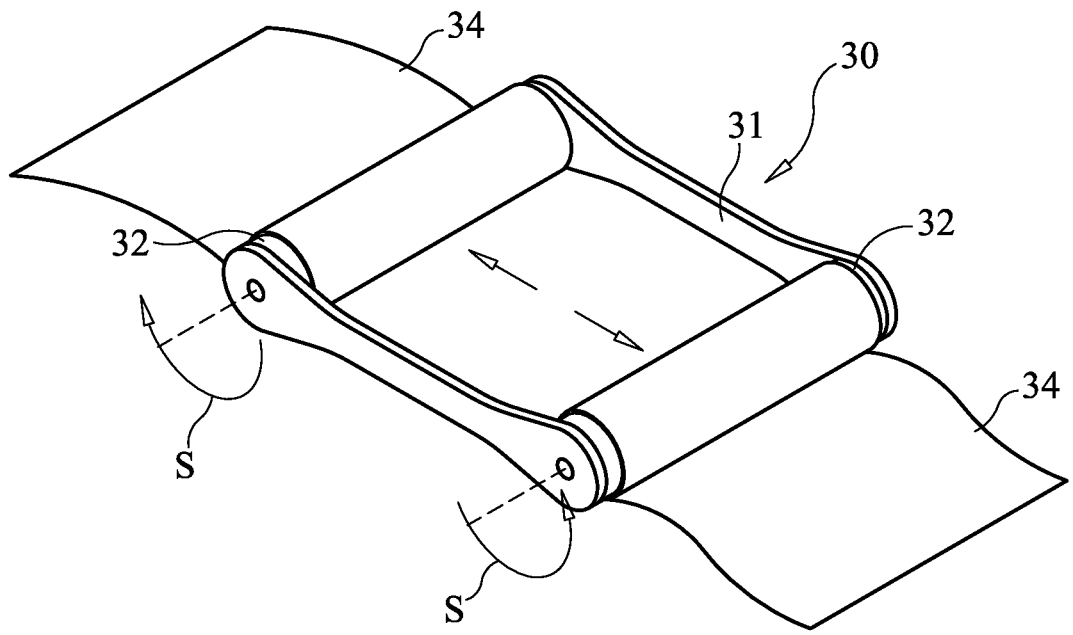
Figure 7:
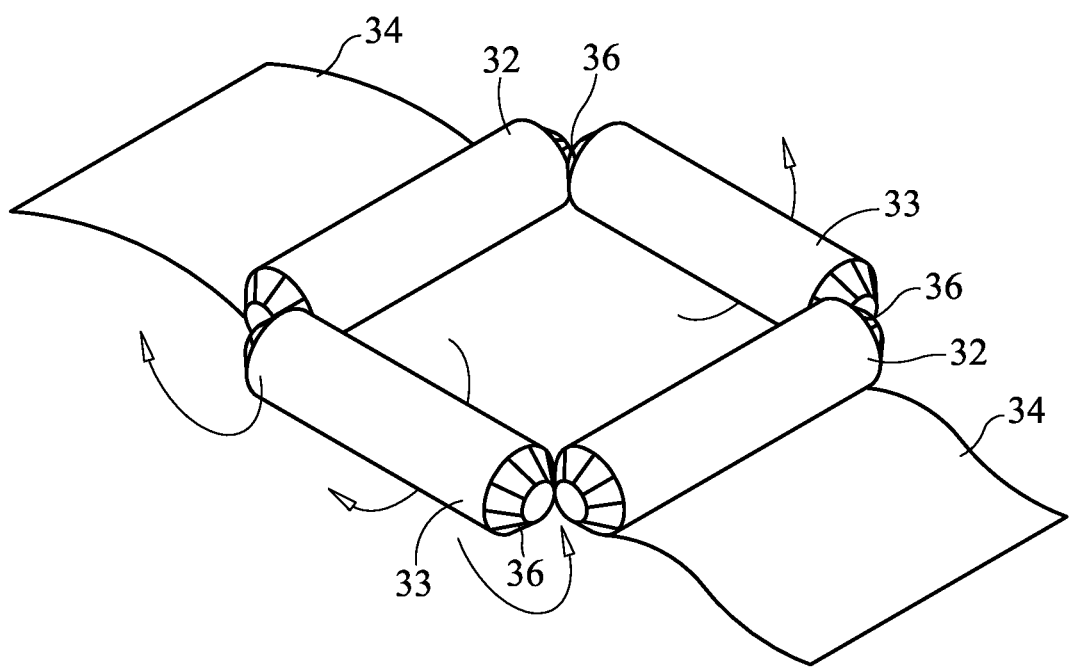
Figure 8A:
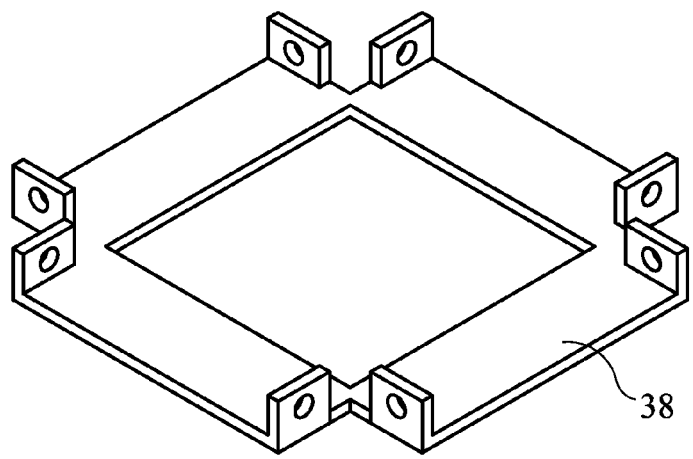
Figure 8B:
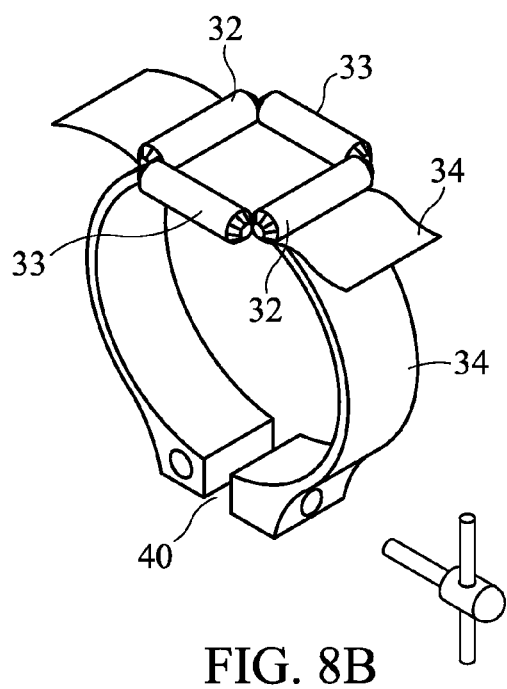
Figure 8C:
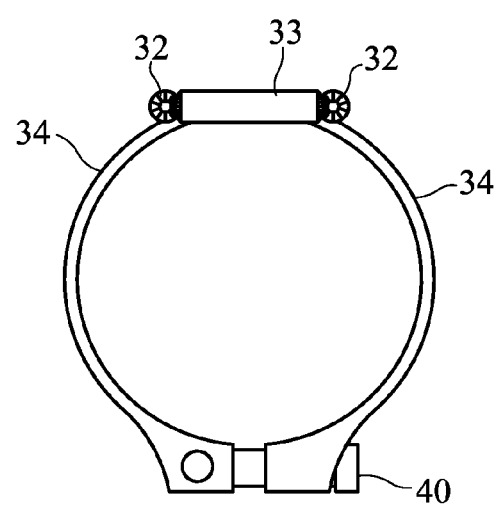

FIGS. 6A-C illustrate sectional views of a skin tensioning and pinching device worn by a user, according to the present invention;

FIG. 7 illustrates a sectional view of a skin tensioning and pinching device worn by a user, according to the present invention; and FIGS. 8A-C illustrate views of a skin tensioning and pinching device worn by a user, according to the present invention.

V. DESCRIPTION OF THE PREFERRED EMBODIMENTS

Figure 1:
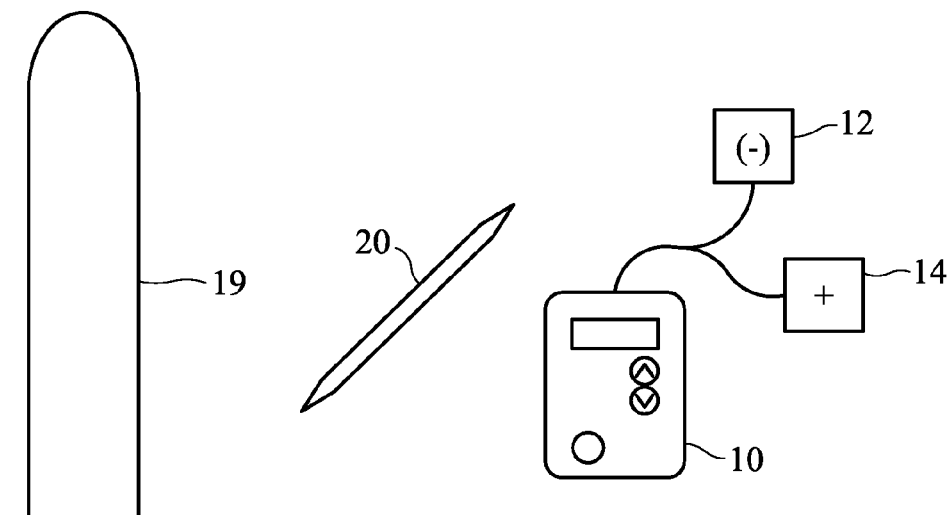
FIG. 1 illustrates a front view of a system for administering pain-free injections according to the present invention.
Figure 2:
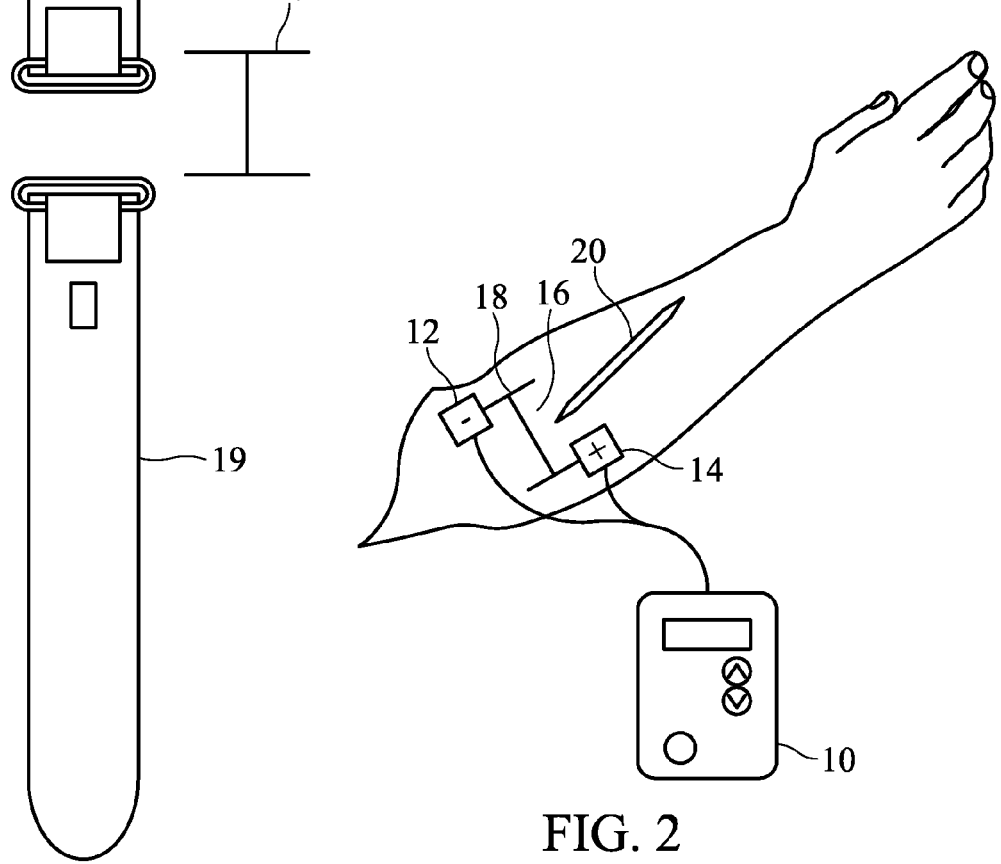
FIG. 2 illustrates a view of the system for administering pain-free injections placed on a user, according to the present invention.

Referring to the drawings, FIGS. 1 and 2 illustrate the system for administering pain-free injections which includes an electric current source 10 having at least two electrodes 12, 14 attached adjacent an injection site 16, the electric current source 10 producing a variable numbness pattern in the injection site 16. The electrodes 12, 14 may be utilized to provide a frame of reference for identifying a plurality of sub-areas of the injection site 16. Alternatively, a fence 18 may be removably applied, such as with a belt or straps 19 or via manual pressure, to the injection site 16 and provides a frame of reference within the injection site 16 for identifying a plurality of sub-areas of the injection site 16. A probe 20 is applied to the plurality of subareas of the injection site 16, and one or more areas of numbness in the variable numbness pattern in the injection site 16 are identifiable according to the sub-areas defined by the electrodes 12, 14 or the fence 18. The electric current source 10 may be a commonly-available transcutaneous electrical nerve stimulation (TENS) device. These TENS devices typically have two to four electrodes. These TENS devices provide a variety of variable electrical outputs, such as wave form, pulse frequency, current, voltage and other parameters. However, regardless of the electric current source selected for use, a common factor in their operation is the unpredictable and variable numbness pattern that is produced. Such unpredictable effects and variability seems to be based on the unique physiology and nerve arrangement and structure of each person using the device, the unique pain tolerance for each user, and our own incomplete knowledge or understanding of pain.

FIG. 2 illustrates a linear, open fence 18 applied to an injection site 16, such as a user's forearm. The fence 18 provides a frame of reference for identifying a plurality of sub-areas of the injection site 16. The linear fence 18 creates a bisected or split field injection site. In use, a single bar extends across the injection site, and cross-bars at each end provide a convenient place to apply manual pressure, or for attachment of a belt 19. The fence will be of a size and shape suitable for defining an area on arms, thighs or posterior regions of an injection recipient. Typical dimensions may be from one-half inch up to 8 inches or more, depending upon the desired application. A fixed or detachable shield wall (see FIG. 4) having a height may be included to prevent a view of the injection site. The probe 20 is applied to the plurality of sub-areas of the injection site 16 and one or more areas of numbness in the variable numbness pattern of the injection site 16 are identifiable according to the sub-areas defined by the fence 18. The probe 20 is used in a methodical manner to test each sub-area of the injection site 16 so as to locate and identify the one or more areas of numbness in the variable numbness pattern produced by the electric current source 10. Once identified, an area of numbness in the variable numbness pattern may be quickly noted with reference to the fence 18 and used as a site for a pain-free hypodermic injection. The probe 20 may be pointed at one or both ends, and may even be sharp enough to cause pain or discomfort if a tested sub-area of the injection site is not numb. This provides a better test before the actual hypodermic needle or syringe is used. In some cases, an actual hypodermic needle may be used as a probe 20. In another embodiment, the probe 20 is a pointed or sharp-ended prod without a syringe. The probe 20 may include a hilt, a tapered, expanding profile or other feature to prevent it from going into the skin too far when trying to locate areas of numbness.

Figure 3:
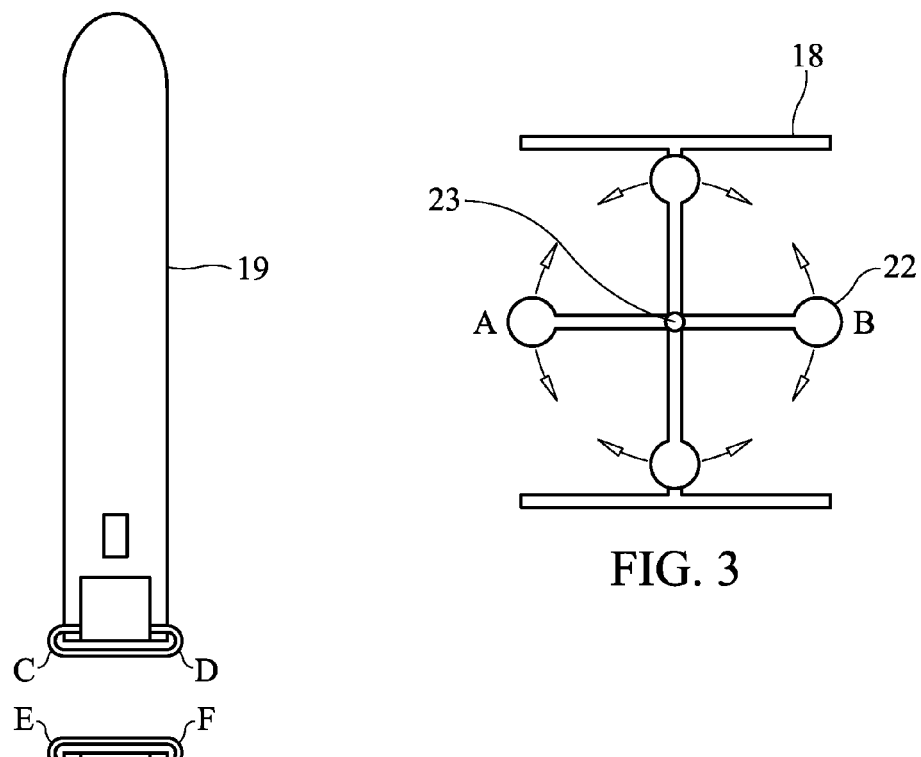
FIG. 3 illustrates a perspective view of a cross-shaped fence for the system for administering pain-free injections, according to the present invention.

FIG. 3 illustrates a perspective view of a cross-shaped fence 22 for use with the system and method for administering pain-free injections. In addition to the utility provided by the linear fence 18 illustrated in FIG. 2, the cross-shaped fence 22 further sub-divides the injection site 16 and thereby provides a more refined ability to locate and identify areas of numbness and the variable numbness pattern of the injection site 16. The cross-shaped fence 22 may be based on the linear fence 18, and may include an axis or pivot-point 23 for rotating the cross-shaped fence 22 and providing a more personalized arrangement according to the variable and unpredictable numbness pattern. Like all fences described herein, this fence 22 may be attached to a band or strap 19.

Figure 4:
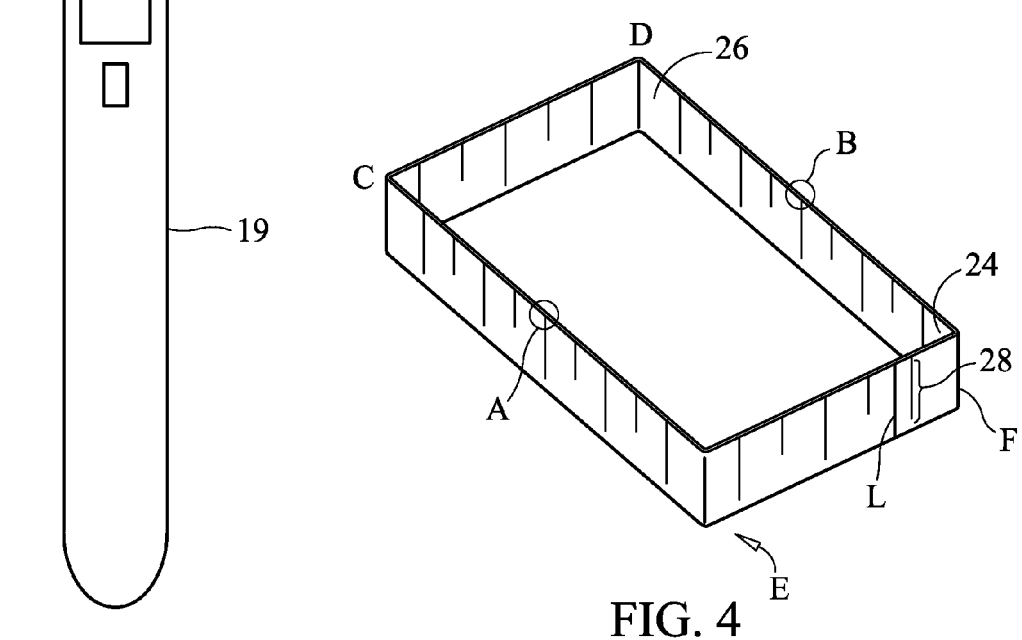
FIG. 4 illustrates a perspective view of a polygonal fence for the system for use in administering pain-free injections, according to the present invention, with marks identifying specific areas and points.

FIG. 4 illustrates a perspective view of a polygonal fence 24. In this example, the polygonal fence 24 is a rectangle, but may be a triangle, hexagon or any other polygonal shape which lends itself to the goal of defining an injection site 16 and which aids in the discovery and use of one or more areas of numbness in the variable numbness pattern. Any of the fences 18, 22, 24 illustrated and described in this application may be applied via manual pressure or via a strap or belt arrangement 19, according to the desired advantages provided by each arrangement and the desired effect sought by a user. FIG. 4 illustrates a graduated scale 26 placed on the fence 24 to provide very positive sub-areas of the injection site 16 for identification of one or more areas of numbness in the variable numbness pattern. The graduations 26 may be applied to any of the fences 18, 22, 24 illustrated and described herein. These graduations 26 may also provide recommended placement for the electrodes 12, 14, or additional notches or other marks may be used to guide the user in electrode placement.

The polygonal fence 24 illustrated in FIG. 4 also includes a shield wall 28 having a defined height which tends to elevate the fence 24 above the injection site 16 and thereby blocks the view of at least part of the injection site from the user. The height of the shield wall 28 may be made in a number of heights within a reasonable range, as would be appreciated by one skilled in the art, in order to permit a user to selectively block his view of the injection site 16 when it is time for administration of an injection, whether self-administration or by another. Fence 16, 22, 24 may include body-conforming contours to aid its placement on an injection site. The fences 16, 22, 24 illustrated herein are generally flat in arrangement, but may be curved or may be made of a flexible material, such as a medical-grade plastic that would allow a user to apply the fence accurately and comfortably on an injection site 16. The fence 16, 22, 24 and probe 20 may be made from medical-grade materials, whether plastics, metals or other suitable materials, which would provide the ability to be sterilized repeatedly without significant degradation and to insure the injection site 16 is appropriately clean and uncontaminated for hypodermic injections.

Figure 5:
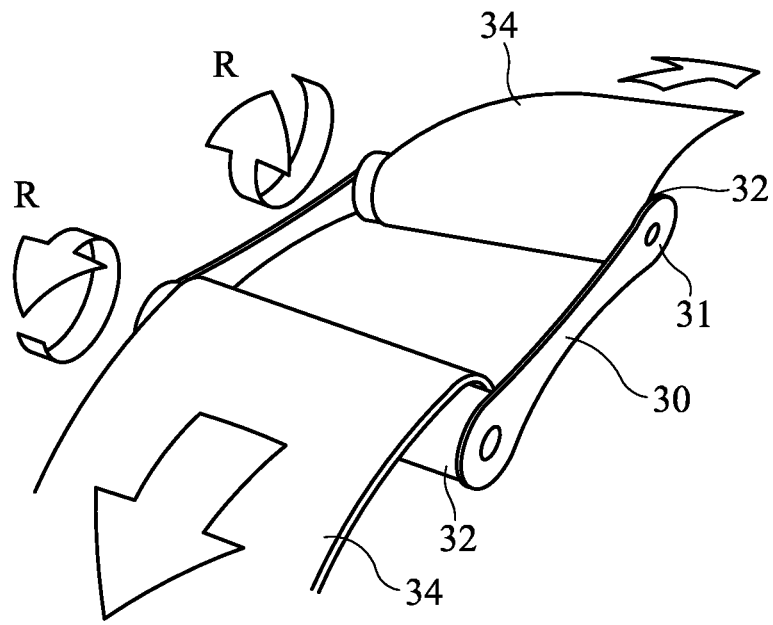
FIG. 5 illustrates a perspective view of a skin tensioning and pinching device for use with the system and method for administering pain-free injections, according to the present invention.

FIG. 5 illustrates a skin tensioning and pinching device 30 for use as a fence for the system and method for administering pain-free injections. It was found that the pushing, folding, bending and pinching of skin by a needle added it own portion of pain and discomfort. A device to apply tension or to pinch the skin may be helpful to eliminate this pain and discomfort, in addition to providing the advantages of a fence. As illustrated in FIG. 5, the tensioning and pinching device 30 includes a polygonal framework 31 similar to the fence 24 in FIG. 4. The tensioning and pinching device 30 includes at least a pair of rollers 32, which are attached to a band 34, which is wound around each roller 32. A spring may be included between the roller 32 and the framework 31 in order to wind the band 34 onto the roller 32. This enhances the ease-of-use of the device 30 and ensures that it is ready to be used quickly, without requiring the band 34 to be manually wound before use. When placed against a user's skin in an injection site 16, tensioning the band 34 would tend to rotate the rollers 32 in the direction R and pinch the skin together in the injection site 16, as illustrated in FIG. 5. However, inverting the pinching and tensioning device 30, as illustrated in FIGS. 6A-6C, would result in the skin in the injection site 16 being pulled taut, or tensioned. FIG. 6A illustrates the inverted device 30 in an untensioned stated. FIGS. 6B-6C illustrate the inverted device with the bands 34 tensioned and rollers 32 rotated in direction S. Each of these techniques may be useful for different types of hypodermic injection procedures.

Additional arrangements for the pinching and tensioning device 30 may be envisioned, such as illustrated in FIG. 7 where two pairs of rollers 32, 33 act in cooperation via an angled gear arrangement 36 where each roller 32, 33 abuts another. This arrangement provides a two-dimensional force distribution in the injection site 16 for more uniform pinching, stretching or tightening of the skin in the injection site 16. The rollers 32, 33 and the belts 34 may have a surface quality, such as texture, bumps, ribs, etc. . . . , that provides a gripping action to permit the belts 34 to push or pull the skin of the injection site in the intended direction. Certain soft or rubbery materials may provide this capability as well. A band 34 may pull on two of the rollers 32 and thereby transfer force directly to the skin of the injection site 16 or transfer the rotational force to the adjoining rollers 33 and thereby apply tension or compression, pushing or pulling, to the skin of the injection site 16.

FIG. 8A illustrates a simple framework 38 that might be used to support a tensioning and pinching device 30 having two pairs of rollers 32, 33, such as is illustrated in FIG. 7. The bands 34 may be tightened or drawn together via a tensioning mechanism 40, such as is illustrated in FIGS. 8B-8C. Tensioning this mechanism 40 would provide the desired pushing or pulling of the skin in the injection site. Preferably, the thickness of the bands 34 and the diameter of the rollers 32, 33 would elevate the framework 38 above the skin, at least slightly, to encourage positive engagement of the bands 34 with the skin.

The system for administering pain-free injections wherein the fence has a pair of parallel rollers 32 rotatably mounted to a framework 38, a window being formed between the rollers 32; and a band 34 having high friction characteristics with skin is wound around each roller 32, wherein tensioning the band 34 with the fence in a first orientation rotates the rollers 32 and pushes the skin in the window together.

The system for administering pain-free injections wherein the fence has two pairs of rollers 32, 33 rotatably mounted to a framework 38, each roller 32, 33 mounted at 90 degrees to each adjacent roller 32, 33, and each roller 32, 33 rotatably engaging each adjacent roller 32, 33, wherein tensioning the band 34 with the fence in the first orientation rotates the rollers 32, 33 and pushes the skin in the window together from two directions, and wherein tensioning the band 34 with the fence in the second orientation rotates the rollers 32, 33 and pulls the skin in the window taut from two directions.

The system for administering pain-free injections wherein the fence has a pair of parallel rollers 33 rotatably mounted to a framework, a window being formed between the rollers; and a band 34 having high friction characteristics with skin is wound around each roller 33, wherein tensioning the band 34 with the fence in a second orientation rotates the rollers 33 and pulls the skin in the window taut.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A system for administering pain-free injections, the system comprising: an electric current source having at least two electrodes attached adjacent an injection site, the electric current source producing a variable numbness pattern; a fence removably applied to the injection site and providing a frame of reference for identifying a plurality of sub-areas of the injection site; and a probe applied to the plurality of sub-areas of the injection site, wherein one or more areas of numbness in the variable numbness pattern are identifiable according to the sub-areas defined by the fence, wherein the fence comprises a pair of parallel rollers rotatably mounted to a framework, a window being formed between the rollers; and a band having high friction characteristics with skin is wound around each roller, wherein tensioning the band with the fence in a first orientation rotates the rollers and pushes the skin in the window together.

2. The system for administering pain-free injections of claim 1, wherein the fence is removably applied to the injection site via the belt.

3. The system for administering pain-free injections of claim 1, wherein the framework is a polygonal framework.

4. The system for administering pain-free injections of claim 1, wherein the fence includes body-conforming contours.

5. The system for administering pain-free injections of claim 1, wherein the fence and probe include medical-grade materials, whether plastics or metals.

6. The system for administering pain-free injections of claim 1, wherein the fence comprises a second pair of rollers rotatably mounted to the framework, each roller mounted at 90 degrees to each adjacent roller, and each roller rotatably engaging each adjacent roller, wherein tensioning the band with the fence in the first orientation rotates the rollers and pushes the skin in the window together from two directions.

7. A system for administering pain-free injections, the system comprising: an electric current source having at least two electrodes attached adjacent an injection site, the electric current source producing a variable numbness pattern; a fence removably applied to the injection site and providing a frame of reference for identifying a plurality of sub-areas of the injection site; and a probe applied to the plurality of sub-areas of the injection site, wherein one or more areas of numbness in the variable numbness pattern are identifiable according to the sub-areas defined by the fence, wherein the fence comprises a pair of parallel rollers rotatably mounted to a framework, a window being formed between the rollers; and a band having high friction characteristics with skin is wound around each roller, wherein tensioning the band with the fence in a second orientation rotates the rollers and pulls the skin in the window taut.

8. The system for administering pain-free injections of claim 7, wherein the fence comprises a second pair of rollers rotatably mounted to a frame, each roller mounted at 90 degrees to each adjacent roller, and each roller rotatably engaging each adjacent roller, wherein tensioning the band with the fence in the second orientation rotates the rollers and pulls the skin in the window taut from two directions.

* * * * *